United States Patent [19]

Pierce et al.

[11] 4,312,920

[45] Jan. 26, 1982

[54] POLYMER ALLOY BLOOD COMPATIBLE SURFACE

[75] Inventors: William S. Pierce, Hummelstown; James H. Donachy, Annville, both of Pa.

[73] Assignee: The United States of America as represented by the Department of Health & Human Services, Washington, D.C.

[21] Appl. No.: 92,102

[22] Filed: Nov. 7, 1979

[51] Int. Cl.³ .......................................... B32B 27/40
[52] U.S. Cl. .................................... 428/425.5; 3/1; 3/1.4; 3/1.7; 128/1 D; 128/214 R; 128/348; 264/255; 264/305
[58] Field of Search ....................... 525/440, 452, 460; 428/425.5; 264/255, 305; 3/1, 1.4, 1.7; 128/1 D, 214 R, 348

[56] References Cited

U.S. PATENT DOCUMENTS 3,246,048 4/1966 Haluska .............................. 525/460
3,562,352 2/1971 Nyilas ................................. 525/460
4,057,595 11/1977 Rauner ............................... 525/460

OTHER PUBLICATIONS

Ward et al., "Production of Biomedical Polymers, In Organometallic Polymers", 1978, Academic Press Inc., New York, pp. 219-229.
Kolobow et al., "Superior Blood Compatibility of Silicone Rubber Free of Silica Filler in the Membrane Lung", Trans. Amer. Soc. Artif. Int. Organs, 1974, vol. XX, pp. 269-277.
Boretos et al., "Surface and Bulk Characteristics of a Polyether Urethane for Artificial Hearts", In J. Biomed. Mater. Res., vol. 9, 1975, pp. 327-340.
Baier, "Key Events in blood Interactions at Nonphysiologic Interfaces-A Personal Primer", Artificial Organs, vol. 2, No. 4.
Wilkes, "Necessary Considerations for Selecting a Polymeric Material for Implanting with Emphasis on Polyurethane", Poly. Sci. & Tech., vol. 8, pp. 45-75

Primary Examiner—James H. Derrington
Attorney, Agent, or Firm—John S. Roberts, Jr.

[57] ABSTRACT

A blood contacting layer and a blood contacting interface consisting of a solvent cast polyurethane alloyed with a filler-free silicone rubber. In the above, the alloy interface comprises an interpenetrating polymer network consisting of polyurethane and filler-free silicone rubber at the molecular level. The process or method of making the layer consists of preheating a metal mold such as an aluminum mold and filling it with a wax. After the wax form is removed, polished and cleaned, it is dipped first in a filler-free silicone rubber which is cured. It is then dipped in segmented polyurethane with curing of 150° F. for about one hour to evaporate the polyurethane solvent. Multiple dips are utilized up to 5 or 7 for implementing the polyurethane. The form containing both silicone rubber and polyurethane is finally cured for a day or 24 hours at about 150° F. and the wax form is removed. Finally, the silicone rubber lining is removed, leaving the binary alloy blood contacting surfaced polyurethane sac.

3 Claims, 8 Drawing Figures

POLYMER ALLOY BLOOD COMPATIBLE SURFACE

The invention described herein was made in the course of work under a grant or award from the Department of Health, Education and Welfare.

This invention relates to a blood contacting layer and a blood contacting interface consisting of a segmented polyurethane alloyed with a filler-free silicone rubber. In the above, the alloy comprises an interpenetrating polymer network consisting of polyurethane and filler-free silicone rubber at the molecular level. The process or method of making the layer consists of preheating a metal mold such as an aluminum mold and filling it with wax. The wax form is removed, polished, cleaned and then dipped first in a filler-free silicone rubber and cured. Then the form is dipped in segmented polyurethane solution with solvent evaporation at 150° F. for about one hour. Multiple dips are utilized up to 5 or 7 to provide the desired thickness of the polyurethane. After the wax form is removed and cleaned, it is dipped. The form containing both silicone rubber and polyurethane is finally cured for a day or 24 hours at about 150° F. and the wax form is removed. Finally, the silicone lining is removed, leaving the binary alloy blood contacting surface.

At or very close to the interface, experiments have shown that most of the silicone rubber is congregated in the molecular alloy and that there is very little silicone rubber away from the direct blood contacting surface that is in the bulk polymer or external surface. It has been calculated that 99.9% or thereabouts of the silicone rubber present is present in the area delimited by a maximum of 40 microns from the blood contacting surface, In this area, by weight percent, the silicone rubber percentile may be as high as 50 to 75%.

The present application is targeted to a method and resulting product of a blood contacting surface, which at the point of contact is a modified segmented polyurethane. The term segmented polyurethane is now well established (cf. Boretos, J. W. and Pierce, W. S., Segmented Polyurethane—*A New Elastomer for Biomedical Application,* Science, 158:1481, 1967). The term segmented polyurethane applies to a transparent polyether type polymer with no plasticizers or fillers and has been described as containing alternating hard segments (HS) and soft segments (SS). It appears that the polyurethane solvent (in this case, N—N dimethyl acetamide but similar effects are broadened with other organic solvents and chemically related solvents such as formamide, tetrahydrofuran, etc.) has a modifying effect on the filler-free silicone rubber and permit the migration of the polyurethane and silicone rubber species. The interface of the present material is known as an interpenetrating polymer network (IPN). As such, there is a migration across the barrier of molecular species from the second component; namely, silica-free silicone rubber. The resulting product is not a mixture nor a copolymer, and the IPNs have been described in the literature as in *Polymer Science and Technology,* Volume 10, "Polymer Alloys" edited by Daniel Klempner and Court C. Frisch (1977) in the preface at page v. It is of some importance that the actual blood contacting surface, which is our preferred modus is achieved by adding and removing a silicone polymer by interpenetration provides a polymer alloy blood compatible surface consisting of the filler-free silicone rubber alloy to a segmented polyurethane.

The development of segmented polyurethanes and the addition of some type of silicone rubber to modify the aspects deleterious to blood contacting surface is about 10 years old. The polyurethanes themselves have good rubber qualities, but poorer blood contacting properties than pure filler-free silicone rubber. The polyurethanes, for example, are illustrated by Biomer (Johnson & Johnson, a bipolymer) and previously Lycra (DuPont, a spandex fiber of polyurethane). The silicone rubber which does not have the desired elastomeric properties of polyurethane, however, does have excellent blood contacting properties probably due to the utilization of dimethyl silicone rubber and the methyl groups close to the surface. It has been found that solvent cast polyurethane cured in juxtaposition to filler-free silicone rubber yields desired alloys and not mixtures or polymers.

It has been found that with the present alloy, 50 to 75% of the dimethyl silicone rubber is crowded very close to the blood contacting layer toward an area up to 40 microns from the actual contact line.

Prior Art Statement

U.S. Pat. No. 3,562,352 to Nyilas, Avco Corporation, describes block copolymers of polyurethane and polysiloxane. It is noted in the Abstract that both polyether and polyester polyurethanes may be utilized.

Transactions American Society of Artificial Internal Organs, Volume 20, 1974, page 269, T. Kolobow et al, entitled "Superior Blood Compatibility of Silicone Rubber Free of Silica Filler in the Membrane Lung."

J. Biomed. Mater. Res., Vol. 9, pp. 327–340 (1975), John W. Boretos, William S. Pierce, Robert E. Baier, Andre F. Leroy and Howard J. Donachy entitled "Surface and Bulk Characteristics of a Polyether Urethane for Artificial Hearts."

Artificial Organs, Vol. 2, no. 4, page 1, Robert E. Baier, entitled "Key Events in Blood Interactions at Nonphysiologic Interfaces—a Personal Primer."

Organometallic Polymers, 1978, Academic Press, Inc., New York, pp, 219–229.

Polymer Science and Technology, Vol. 8, pp. 45–75, Garth L. Wilkes, entitled "Necessary Considerations for Selecting a Polymeric Material for Implantation with Emphasis on Polyurethane."

Products claiming relationship to the above patent, U.S. Pat. No. 3,562,352, are marketed by Roche under the tradename Avcothane. The purpose of the Avcothane and the patent was to combine the good elastomeric properties of the segmented polyurethane with the good blood contacting properties of the silicone rubber.

The surfaces and polymers of the present invention may be presently used as surfaces in artificial hearts and heart assist pumps. In addition, the following uses for the novel layers are closely linked to the aforesaid artificial hearts and ventricular assist pumps; namely, intravenous catheters, blood oxygenators, heart lung machine tubing, inter-aortic balloon pumps and artificial blood vessel grafts.

PROCESS

Figure 1:
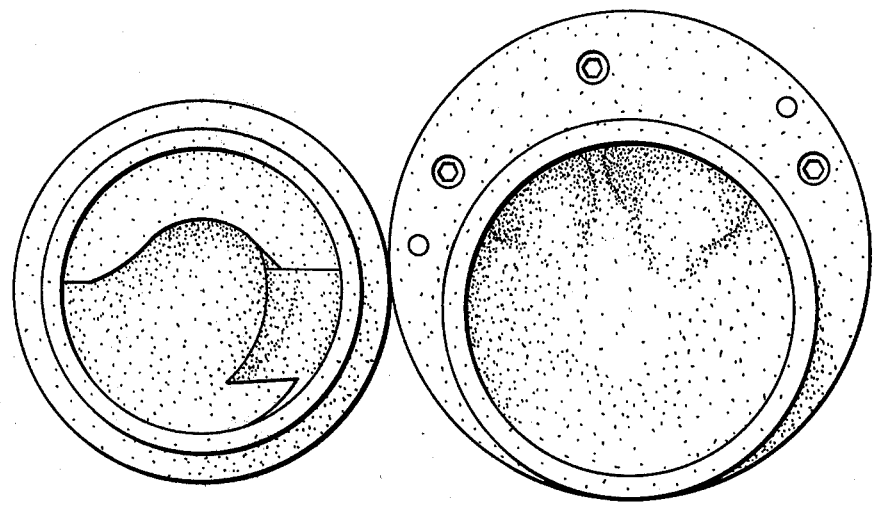
FIG. 1 shows two mold halves ready for assembly and pouring of hot wax.
Figure 2:
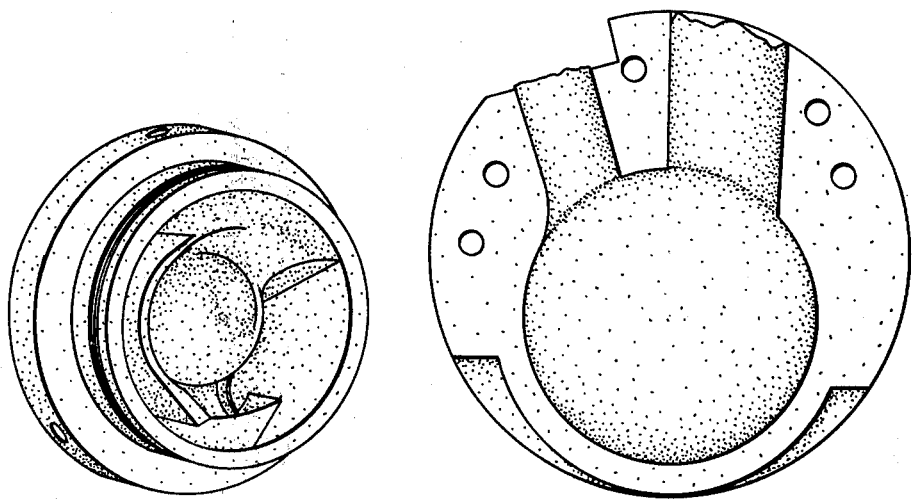
FIG. 2 shows the molds separated and the wax form ready for removal.

A preferred process for the production of the polymers, layers and the surfaces is as follows:

Step I—refer to FIG. 1. An aluminum mold was preheated to a desired temperature of 270° to 300° F. and then hot wax was poured (Epolene C10, which is a low molecular weight polyethylene resin of Shell Chemical Co.) in a preheated mold, filling completely. The mold was allowed to cool until the desired wall thickness jelled. Then, excess wax was poured from the form. The form is then cooled to room temperature. The hollow wax form was removed from the mold. See FIG. 2.

Figure 3:
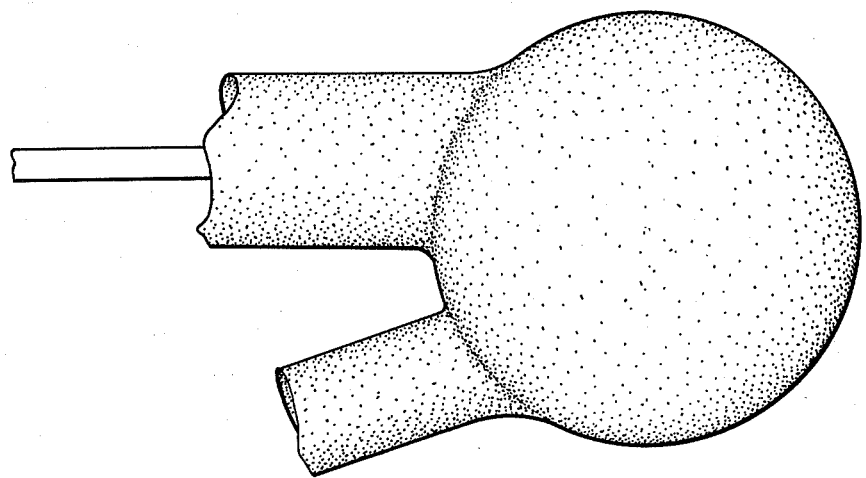
FIG. 3 shows a hollow form as removed from the mold.
Figure 4:
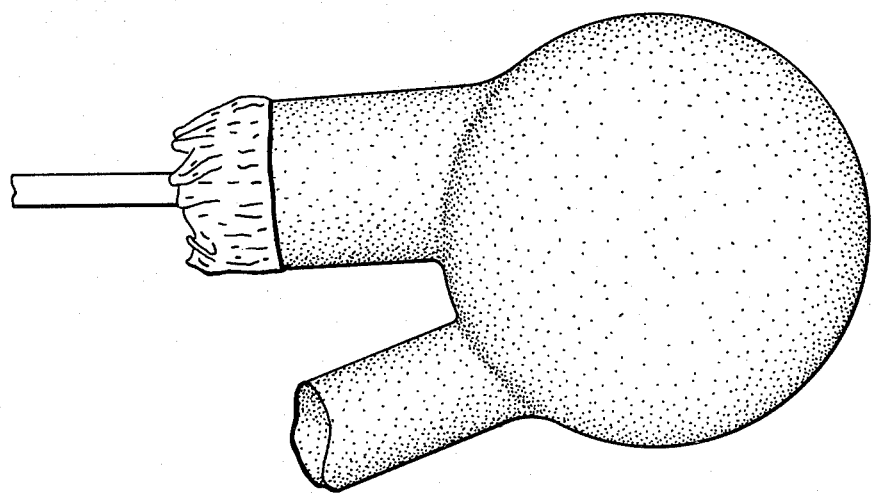
FIG. 4 shows a sanded and polished wax form ready for dipping in filler-free silicone rubber.

Step II—refer to FIG. 3. The wax form was removed from the mold with flash lines and slight imperfection. The form was sanded and fine polished to accomplish as smooth a surface as possible. FIG. 4 shows the sanded and polished form.

Figure 5:
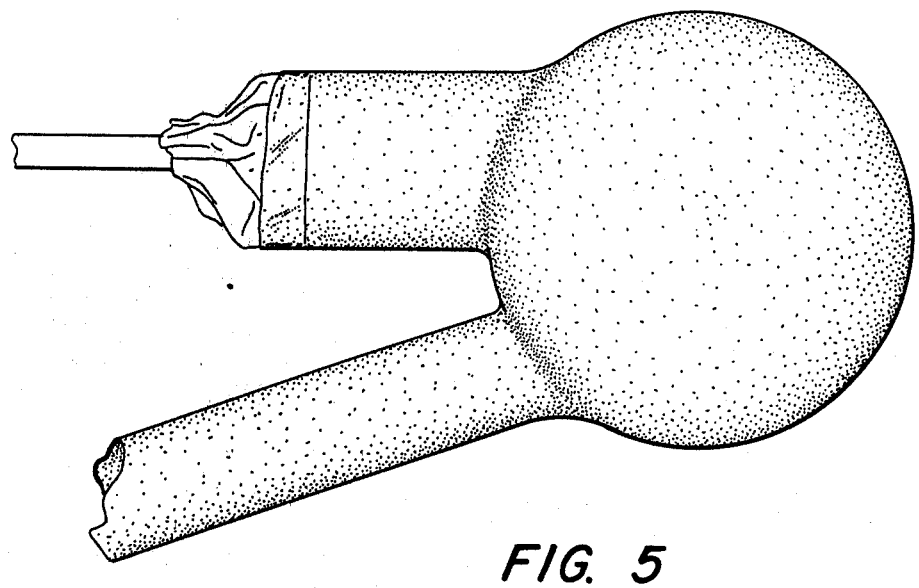
FIG. 5 shows the form subsequently coated with a layer of filler-free silicone rubber.

Step III—the form was cleaned with a lower alkanol (propyl alcohol) and dried with deionized air. The form was kept in a laminar flow air hood and dipped in filler-free silicone rubber. The cure took 4 hours or longer. This step blended the surface giving a high gloss and a non-adhering surface for the polyurethane to be coated against. FIG. 5 shows the clear coating of filler-free silicone rubber on the wax form.

Figure 6:
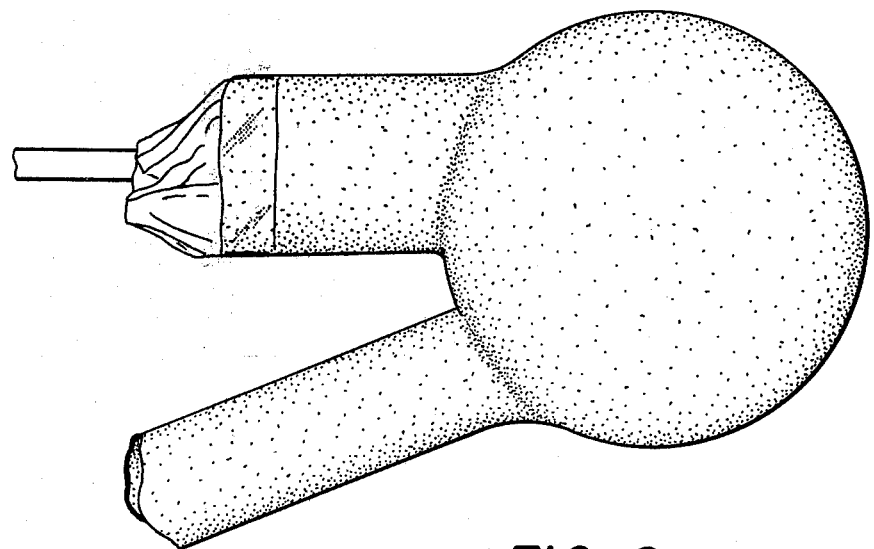
FIG. 6 shows the form coated with 5-7 layers of polyurethane, depending upon the required sac thickness.

Step IV—the form was then dipped in segmented polyurethane solvent and cured on a rotisserie at 150° F. for 1 hour. This process was repeated until the desired sac thickness was acquired. Normally, this required 5 to 7 dips. FIG. 6 shows this step when completed.

Figure 7:
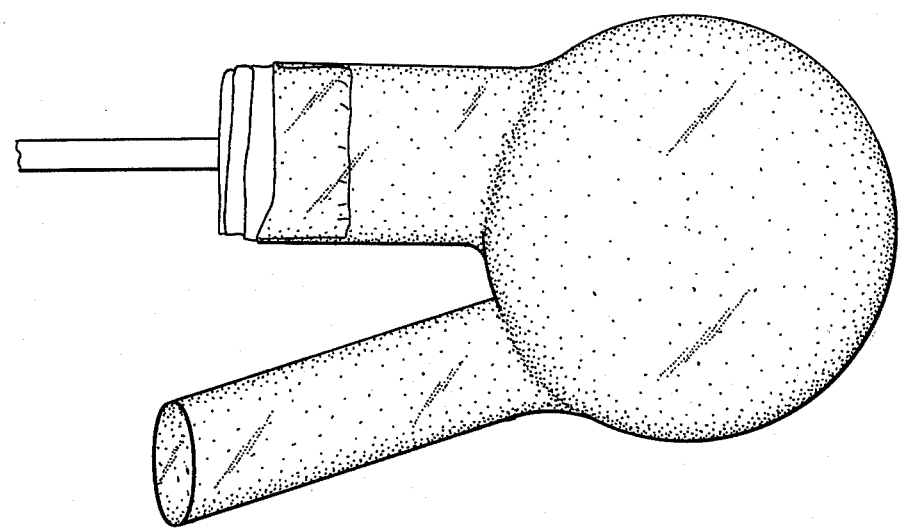
FIG. 7 shows the sac after removal of the wax form and silicone rubber contacting surface.
Figure 8:
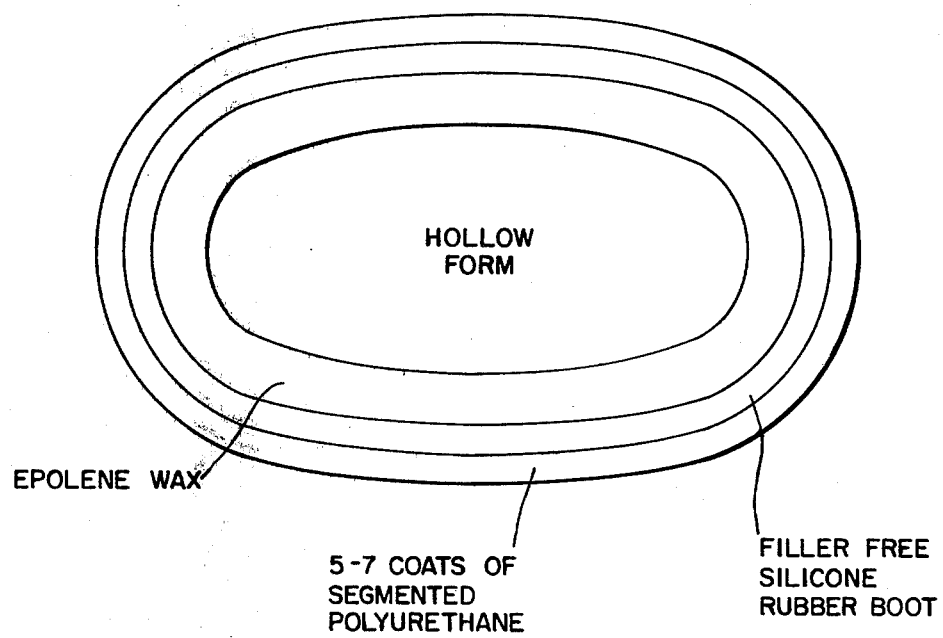
FIG. 8 is a cross-section of the sac showing the epolene wax, the filler-free silicone rubber boot and 5-7 coats of segmented polyurethane to provide the desired sac thickness.

Step V—The form was then placed in a circulating oven for 24 hours at a curing temperature of 150° F. After curing, the wax form was crushed into pieces by hand pressure and removed from inside of the sac. The filler-free silicone lining (boot) was then removed, leaving an internal sac surface that is a blood contacting surface (FIG. 7). The blood sac was then fitted into a rigid case of a blood pump.

We claim:

1. A blood contacting polyurethane layer having only one of its surfaces modified by alloying silicone rubber on only that modified surface and completely contained within 40 microns of said surface.

2. The blood contacting polyurethane layer according to claim 1 which comprises a segmented polyurethane alloyed with a filler-free silicone rubber.

3. A blood contacting polyurethane according to claim 1, wherein said alloying is a segmented polyurethane with an interpenetrating amount of a filler-free silicone rubber.

* * * * *